(12) United States Patent
Fujita et al.

(10) Patent No.: US 9,266,106 B2
(45) Date of Patent: Feb. 23, 2016

(54) MICRO-CHANNEL CHIP

(71) Applicant: National University Corporation Shimane University, Matsue-shi, Shimane (JP)

(72) Inventors: Yasuhisa Fujita, Matsue (JP); Haruo Takeshita, Izumo (JP); Junko Fujihara, Izumo (JP); Yutaka Fukui, Izumo (JP); Mari Tabuchi, Tokyo (JP)

(73) Assignee: NATIONAL UNIVERSITY CORPORATION SHIMANE UNIVERSITY, Matsue-Shi, Shimane (JP)

( * ) Notice: Subject to any disclaimer, the term of this patent is extended or adjusted under 35 U.S.C. 154(b) by 0 days.

(21) Appl. No.: 14/380,602

(22) PCT Filed: Feb. 25, 2013

(86) PCT No.: PCT/JP2013/054700
§ 371 (c)(1),
(2) Date: Aug. 22, 2014

(87) PCT Pub. No.: WO2013/125715
PCT Pub. Date: Aug. 29, 2013

(65) Prior Publication Data
US 2015/0027893 A1    Jan. 29, 2015

(30) Foreign Application Priority Data
Feb. 23, 2012   (JP) ................................ 2012-037582

(51) Int. Cl.
| | |
|---|---|
| *G01N 27/453* | (2006.01) |
| *B01L 3/00* | (2006.01) |
| *G01N 21/05* | (2006.01) |
| *G01N 21/64* | (2006.01) |
| *G01N 27/447* | (2006.01) |
| *G01N 21/03* | (2006.01) |

(52) U.S. Cl.
CPC ......... *B01L 3/502715* (2013.01); *B01L 3/5027* (2013.01); *G01N 21/05* (2013.01);
(Continued)

(58) Field of Classification Search
CPC ............ B01L 3/5027; B01L 3/502707; G01N 27/44791
See application file for complete search history.

(56) References Cited

U.S. PATENT DOCUMENTS

| | | | |
|---|---|---|---|
| 6,488,831 B1 * | 12/2002 | Hayes | ............................ 204/454 |
| 2003/0113713 A1 | 6/2003 | Glezer et al. | |
| 2011/0281267 A1 * | 11/2011 | Carbone et al. | .............. 435/6.11 |

FOREIGN PATENT DOCUMENTS

| | | |
|---|---|---|
| JP | 2005-140683 A | 6/2005 |
| JP | 2005-172773 A | 6/2005 |

(Continued)

OTHER PUBLICATIONS

S. B. Desu Ultra-thin TiO2 films by a novel method, Materials Science and Engineering, B13 (1992) 299-303.*

*Primary Examiner* — Alex Noguerola
(74) *Attorney, Agent, or Firm* — Birch, Stewart, Kolasch & Birch, LLP (57) ABSTRACT

A convenient technique allows detecting fluorescence emitted in the channel with a uniformly high detection sensitivity and a good reproducibility. On the front face side of a plate-like body 11, a groove-shaped introduction channel 12 and separation channel 14 are formed. In this micro-channel chip 10, on the inner faces of a groove constituting the separation channel 14 formed in a surface of the plate-like body 11, there is formed a fine particle layer 20 provided by sintering fine particles having an average particle diameter of 10 to 500 nm mainly composed of zinc oxide (ZnO) or titanium oxide ($TiO_2$).

7 Claims, 12 Drawing Sheets

(52) U.S. Cl.
CPC ........... *G01N 21/643* (2013.01); *G01N 21/645* (2013.01); *G01N 21/6486* (2013.01); *G01N 27/44704* (2013.01); *G01N 27/44791* (2013.01); *B01L 2400/0415* (2013.01); *G01N 2021/0346* (2013.01); *G01N 2021/058* (2013.01); *G01N 2021/6482* (2013.01); *G01N 2201/061* (2013.01)

(56) References Cited

FOREIGN PATENT DOCUMENTS

| | | |
|---|---|---|
| JP | 2005-207860 A | 8/2005 |
| JP | 2008-233051 A | 10/2008 |
| JP | 2009-142283 A | 7/2009 |

\* cited by examiner

MICRO-CHANNEL CHIP

TECHNICAL FIELD

The present invention relates to a structure of a micro-channel chip for use in such applications as electrophoresis in which a buffer liquid mixed with a sample to be analyzed is electrophoretically migrated.

BACKGROUND ART

The electrophoresis method is extremely effective in analyzing DNA, a protein expressed in cancer, and the like, from a micro amount of blood which has been collected from a subject. With the electrophoresis method, a sample (blood, or the like) added with a fluorescent dye is mixed into a buffer liquid containing a gel. Thereafter, this liquid is supplied to one end of a channel (micro-channel) having a fine cross-sectional area, and a voltage is applied across both ends of the channel, then, the charged molecule is gradually migrated toward the other end in the channel by the electric field, however, the greater the molecular weight of a molecule, the slower the migration speed therefore will be. Therefore, after the lapse of a predetermined time, the reaching position (migration distance) of each particular type of molecule varies in a long channel.

In order to determine this migration distance, the sample is mixed with a specific fluorescent dye, and this fluorescent dye is carried by a molecule, DNA, or the like, which is to be analyzed. This fluorescent dye, when irradiated with an excitation light, emits fluorescence having a specific wavelength (color) which is longer than that of this excitation light, and therefore, by examining the distribution of this fluorescence in the channel after the lapse of a predetermined time, the migration distance can be measured. Thereby, it is possible to perform, for example, composition analysis of a molecule or DNA contained in the sample, and the like. Thus, in order to perform an analysis with high sensitivity, there is the need for a technique which allows fluorescence in the fine channel to be detected with high accuracy.

For improving the sensitivity of such electrophoresis method, Patent Document 1 discloses a technique with which the channel is covered with a diffraction grating having a light scattering function to thereby enhance the efficiency of detection of fluorescence emitted by a fluorescent dye. However, with this method, it is particularly difficult to make the analyzing apparatus including the channel compact.

Contrarily to this, with the method disclosed in Patent Document 2, the configuration of the analyzing apparatus including a micro-channel is the same as that of the conventional one, but the buffer liquid is mixed with ZnO powder (ZnO fine particles) to thereby substantially enhance the intensity of the fluorescence. In this case, the excitation light is multiple-scattered by the colloidal particles formed caused by the ZnO powder, thereby the intensity of the excitation light irradiated on the fluorescent dye molecules being substantially enhanced. In addition, the light corresponding to the forbidden bandwidth of ZnO is ultraviolet radiation, and thus the excitation light on the fluorescent dye and the fluorescence thereof will not be absorbed by the ZnO fine particles. Therefore, the substantial intensity of the fluorescence emitted from the fluorescent dye can be enhanced. By using this method, it is possible to provide a detection sensitivity which is, for example, double or more times as high as that which has been conventionally available.

CITATION LIST

Patent Literature

Patent Document 1: Japanese Patent Application Laid-open No. 2005-172773
Patent Document 2: Japanese Patent Application Laid-open No. 2008-233051

SUMMARY OF THE INVENTION

Problems to be Solved by the Invention

With the method disclosed in Patent Document 2, it is required to use a buffer liquid which is mixed with ZnO powder at a prescribed concentration. Here, there has arisen the need for adjusting the viscosity, and the like, of the buffer liquid in accordance with the sample, and thus, it has become necessary to make an operation of mixing ZnO powder into each particular buffer liquid. In other words, the operation has become extremely complicated.

In addition, an actual electrophoresis measurement is performed using an apparatus with which the operation is automated, and the distribution of fluorescence in the channel is often automatically measured. In this case, the condition of mixing ZnO powder varies depending upon the type of the buffer liquid (viscosity, and the like), and when the buffer liquid is changed over, the degree of fluorescence is also changed, thereby there arising the need for adjusting the apparatus every time, and thus automation of the measurement having been substantially difficult.

Further, for a buffer liquid with a high viscosity, it is not easy to uniformly mix ZnO powder to provide a good reproducibility. Therefore, it has been difficult to uniformly obtain a high detection sensitivity with a good reproducibility.

Accordingly, it has been difficult to use a convenient technique for detecting the fluorescence emitted in the channel at a uniformly high detection sensitivity with a good reproducibility.

The present invention has been made in view of such problems, and it is an object of the present invention to provide solutions to the above-mentioned problems.

Means for Solving the Problems

In order to solve the above-mentioned problems, the present invention has been provided with the following configuration.

The micro-channel chip of the present invention is a micro-channel chip, including a channel, the channel being provided for introducing a liquid containing a fluorescent dye therein, and having a configuration allowing light emitted by the fluorescent dye to be observed from outside, on an inner wall of the channel, there being formed a fine particle layer provided by sintering fine particles having an average particle diameter of 10 to 500 nm and mainly composed of zinc oxide (ZnO) or titanium oxide ($TiO_2$).

With the micro-channel chip of the present invention, the channel is configured by using a groove formed in a surface of a substrate which is transparent to an excitation light irradiated onto the fluorescent dye.

With the micro-channel chip of the present invention, there is provided a configuration in which an electric field is applied to a liquid in the channel.

With the micro-channel chip of the present invention, the fine particles are mainly composed of ZnO, having been manufactured by evaporating a zinc material by an arc discharge in a chamber provided with a reduced pressure oxygen atmosphere and then synthesizing them.

With the micro-channel chip of the present invention, the wavelength of the excitation light irradiated onto the fluorescent dye is in the range of 400 to 500 nm, and the average particle diameter of the fine particles is in the range of 400 to 500 nm.

Advantages of the Invention

The present invention is configured as described above, thereby providing a convenient technique which allows detecting of fluorescence emitted in the channel at a uniformly high detection sensitivity with a good reproducibility.

BEST MODE FOR CARRYING OUT THE INVENTION

The configuration of a micro-channel chip according to an embodiment of the present invention is the same as that which is disclosed in Patent Document 2. However, a different point is that the fine particles are fixed on the inner faces of the channel, and instead of this fixation, in the buffer liquid used in the embodiment of the present invention, no fine particles are mixed. In other words, when such micro-channel chip is used to perform electrophoresis, a buffer liquid which is generally used can be adopted as it is.

Figure 1A:
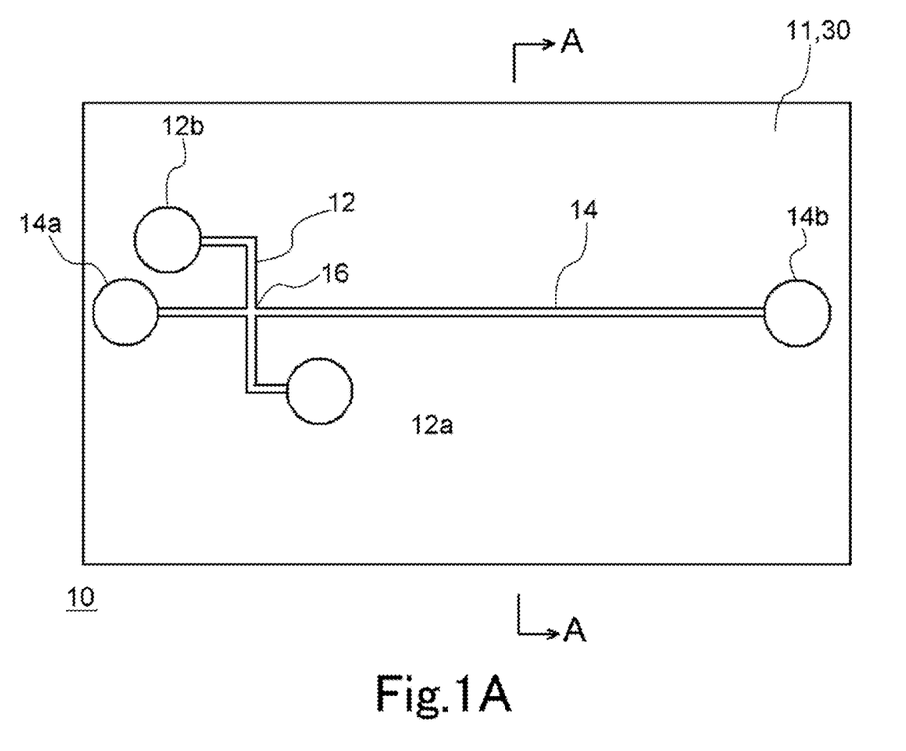
FIGS. 1(a), 1(b), and 1(c) are a plan view, a sectional view, and a partially enlarged sectional view thereof, respectively, illustrating a configuration of a micro-channel chip according to an embodiment of the present invention.
Figure 1B:
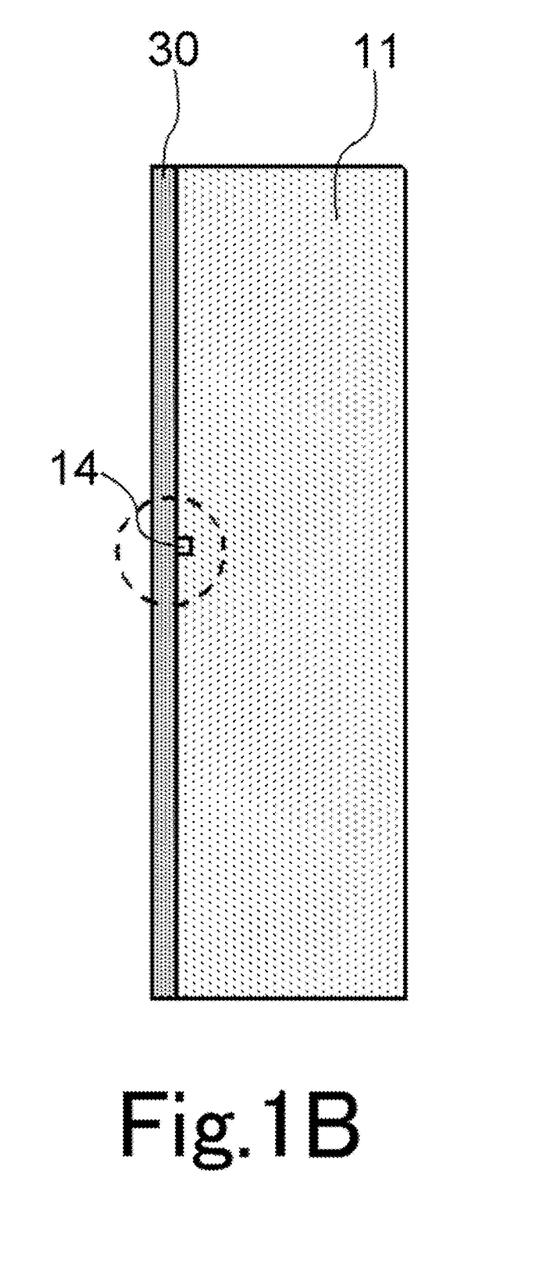
Figure 1C:
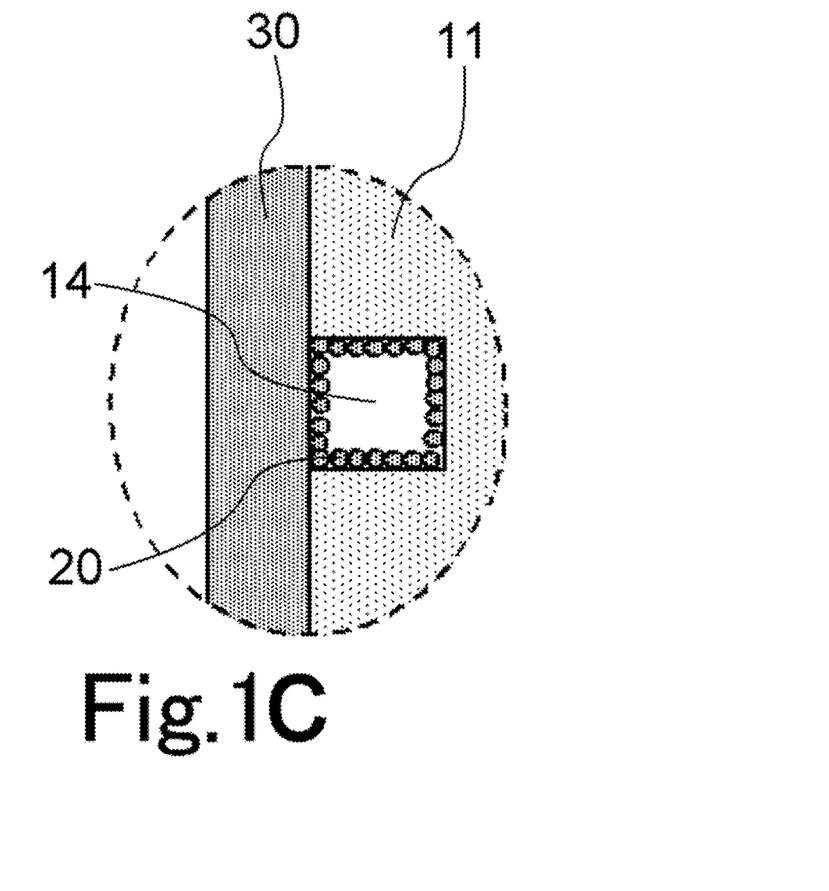

FIG. 1 (a) is a plan view showing a configuration of such micro-channel chip 10; FIG. 1 (b) is a sectional view along a direction of AA; and FIG. 1 (c) is an enlarged view of a portion encircled with a dotted line in the sectional view. The geometrical shape of such micro-channel chip 10 is the same as that of the microchip disclosed in Patent Document 2. The micro-channel chip 10 has a transparent plate-like body 11 as a substrate that is substantially rectangular in planar shape. For the size, an appropriate value can be selected in accordance with the design, however, for example, the length in a longitudinal direction is 10 to 120 mm or so, while the length in a crosswise direction is 10 to 120 mm or so, and the thickness is 0.5 to 5 mm or so.

Inside of the plate-like body 11, an introduction channel 12 and a separation channel 14 which have a groove-like geometry are formed. The introduction channel 12 and the separation channel 14 intersect with each other at right angles at an intersection portion 16. In other words, the introduction channel 12 and the separation channel 14 intersect with each other in a planar shape of a cross.

To both upper and lower ends of the introduction channel 12, a sample reservoir 12a and an outlet 12b, which are formed by digging a surface of the plate-like body 11 in a substantially circular shape, are connected, respectively. Also, to both ends of the separation channel 14, a buffer injection port 14a and a buffer storage hole 14b, which are formed by digging a surface of the plate-like body 11 in a substantially circular shape, are connected, respectively. Further, to the surface of the plate-like body 11, a lid 30, which is formed of a glass, or the like, is joined. The introduction channel 12 and the separation channel 14 are covered with this lid 30, and in locations of the sample reservoir 12a, the outlet 12b, the buffer injection port 14a, and the buffer storage hole 14b, the lid 30 is opened.

The introduction channel 12 is constituted by a channel having a uniform width and depth that is formed in the surface of the micro-channel chip 10, being covered with the lid 30. The introduction channel 12 has a crossing groove portion which is linear, intersecting with the separation channel 14, and distal end groove portions which extend straight from both ends of the crossing groove portion mutually in opposite directions which each intersect with the crossing groove portion at right angles thereto.

In performing electrophoresis, an electrophoresis buffer liquid (hereinafter, to be simply referred to as "a buffer liquid") is filled into the introduction channel 12. The details of this buffer liquid will be described later. The introduction channel 12 is used to transfer a sample which has been introduced in the sample reservoir 12a to the intersection portion 16.

The overall length of the introduction channel 12 is specified to be a length which allows a necessary and sufficient quantity of sample for the electrophoresis analysis to be transferred to the intersection portion 16, being normally in the range of 2 to 30 mm, and being, for example, 7 mm or so.

The width of the introduction channel 12 (the width perpendicular to the longitudinal direction of the groove) is normally 50 to 100 µm or so, being, for example 100 µm or so. The depth thereof (the depth of the groove) is normally 10 to 100 µm or so, being, for example approx. 30 µm or so.

The diameter of the sample reservoir 12a and outlet 12b when viewed from top is normally 0.05 mm to 5 mm, being, for example, 3 mm or so. The diameter is specified as appropriate in consideration of the ease of introduction of the sample.

The separation channel 14 is constituted by a channel having a uniform width and depth that is covered with the lid 30. The separation channel 14 intersects with the introduction channel 12 at right angles thereto at the intersection portion 16, being formed to have an overall length longer than that of the introduction channel 12. In the separation channel 14, the buffer liquid is filled. The separation channel 14 is used to electrophorese the sample existing in the intersection portion 16 toward the buffer storage hole 14b. The length of the separation channel 14 (the length between the buffer injection hole 14a and the buffer storage hole 14b in FIG. 1) is specified to be a length which would allow confirmation of the differences in migration distance therein that vary depending upon the molecular weights, and the like, of the substance to be analyzed, being, for example, approx. 4.5 cm or so.

Here, the distance over which the sample is electrophoresed, in other words, the length of the separation channel 14 from the intersection portion 16 to the buffer storage hole 14b is defined as the "separation length". At this time, the length of the separation length is typically specified to be 1 to 5 cm or so, being, for example, approx. 3 cm or so. In order to enhance the resolution of the molecular weight, and the like, it is preferable that the separation length be long, however, increasing the separation length will extend the electrophoresis time, thereby requiring a longer measurement time. Therefore, depending upon the object to be measured, or the resolution requirement, this length is specified as appropriate.

The width and depth of the separation channel 14 are the same as those of the aforementioned introduction channel 12, while the size of the buffer injection port 14a and buffer storage hole 14b is the same as that of the aforementioned sample reservoir 12a and outlet 12b.

Further, the micro-channel chip 10 is configured such that, in the state in which the buffer liquid has been introduced in the introduction channel 12 and the separation channel 14, a potential gradient (an electric field) is formed in the buffer liquid in the introduction channel 12 and that in the separation channel 14. Therefore, although not shown, an electrode for allowing a voltage to be applied thereto is provided in the sample reservoir 12a, the outlet 12b, the buffer injection port 14a, and the buffer storage hole 14b, respectively.

As the material for the plate-like body 11, a material is used which allows the above-mentioned structure (the introduction channel 12, the separation channel 14, and the like) to be formed therein; a later-described fine particle layer 20 to be formed on the inner wall thereof; and will not be eroded by the buffer liquid, and the like. For example, polymethacrylate, fused silica, borosilicate glass, soda glass, polymethyl methacrylate, polycarbonate, dimethylsiloxane, polyethylene terephthalate, and the like, can be used. In order to allow the excitation light (a visible light) to be irradiated from the bottom face side in FIG. 1, it is preferable that the plate-like body 11 be transparent to the excitation light to be irradiated thereon.

As shown in FIG. 1 (c), which is an enlarged view of the section, in this micro-channel chip 10, on the inner faces of a channel constituting the separation channel 14 formed inside of the plate-like body 11, there is formed the fine particle layer 20 which is provided by sintering fine particles having an average particle diameter of 10 to 500 nm and being mainly composed of zinc oxide (ZnO) or titanium oxide ($TiO_2$). The average particle diameter of the fine particles is measured by, for example, the method specified in JIS Z8901. ZnO and $TiO_2$ are preferably used because they have a great forbidden band width, being transparent to the excitation light irradiated onto the fluorescent dye added to the sample, and the fluorescence emitted by this fluorescent dye (either of these types of light is visible), and have a great refractive index, thereby providing a great effect of scattering the light. In addition, ZnO has a crystal structure of wurtzite type, while $TiO_2$ has that of rutile type, or the like, and thus the surfaces of the fine particles of either ZnO or $TiO_2$ are in the form which easily multiple-reflect the light.

In order to form the fine particle layer 20, for example, a coating liquid in which such fine particles are mixed with a solvent, and the like, is first prepared. Specifically, for example, into an aqueous solution in which pure water is mixed with polyacrylic acid, powder comprised of such fine particles is mixed, and an ultrasonic wave is applied thereto. Thereafter, this coating liquid is coated onto the surface of the plate-like body 11 worked to a form shown in FIG. 1, and dried at a low temperature of, for example, 100° C. or so, before being subjected to calcination at a temperature of 300° C. or so for sintering. By repeating this process from coating to calcination a desired number of times, the thickness of the fine particle layer 20 formed on the surface can be adjusted. In this case, the fine particles are fixed not only on the inner faces of the separation channel 14, but also on those of the introduction channel 12, sample reservoir 12a, and the like, however, such fixation presents no problems in performing electrophoresis. If there arises the need for removing the fine particles on the inner faces of the portions other than the separation channel 14, such as the sample reservoir 12a, the fine particles in the portions other than the separation channel 14 may be removed by, for example, covering the separation channel 14 with a photoresist layer before performing wet-etching. Alternatively, in the state in which the lid 30 in FIG. 1 is joined, the above-mentioned coating liquid may be poured into the channel, which is followed by calcination to form the fine particle layer 20. In this case, as shown in FIG. 1, the fine particle layer 20 can be formed also on the inner face of the lid 30 that is faced with the channel. The thickness of the fine particle layer 20 is specified as appropriate such that the electrophoretic migration in the separation channel 14 is not adversely affected, and the later-described fluorescence detection sensitivity is at maximum. In the case where the above-mentioned coating liquid is used, such film thickness can also be easily adjusted by changing the concentration of the coating liquid or the number of coating times.

As such fine particles, the ZnO fine particles, the principal ingredient of which is ZnO, will be explained below. The ZnO fine particles are fine particles which are constituted by ZnO having an average particle diameter of 10 to 500 nm or so, and as described in Japanese Patent Application Laid-open No. 2005-60145, have properties which are different from those of a ZnO bulk. The manufacturing method therefore is also described in this publication. Such fine particles can be manufactured by the in-gas evaporation method. Here, as shown in FIG. 1(c), in a chamber, there is installed a target which is formed of zinc (Zn). With the inside of the chamber being provided with a reduced-pressure atmosphere containing oxygen, an arc discharge is generated between the target and an electrode installed in the vicinity thereof in vacuum to thereby evaporate Zn from a target surface. The evaporated Zn is oxidized by oxygen in the atmosphere to become ZnO, thereby depositing onto the inner wall of the chamber as particles, which provide the ZnO fine particles. As the raw material for the target, a zinc ingot which is not high in concentration, for example, 4N (with a purity of 99.99%) can be used. Even in the case where such a low-purity inexpensive ingot is used, the ZnO fine particles provide high-quality ZnO crystals.

Specifically, as the atmosphere in the chamber, for example, an atmosphere consisting of oxygen gas and nitrogen gas mixed in a molar ratio of 4:1, as in the air, can be used. The pressure of this gas atmosphere is reduced to $20 \times 10^3$ Pa or so, at which an arc discharge can be easily generated. At this time, the properties (the particle diameter, and the like) of the ZnO fine particles can be controlled by adjusting the gas composition of the atmosphere, the pressure, the current value of the arc discharge, and the like. However, by further performing a pulverization treatment using a ball mill, or the like, on the ZnO fine particles manufactured by this method, the particle diameter can be further decreased.

For $TiO_2$ fine particles, those which are normally manufactured and commercially available can be used as appropriate.

Next, the buffer liquid will be explained. This buffer liquid is prepared as an aqueous solution containing a hydrophilic gel, being a liquid which is generally used for electrophoresis.

As the material substance for this hydrophilic gel, a substance which is generally used for electrophoresis can be appropriately selected, however, various cellulose derivatives are particularly suitable. More specifically, as the cellulose derivatives, methylcellulose, hydroxymethylcellulose, carboxymethylcellulose, hydroxyethylcellulose, hydroxypropylcellulose (HPC), and hydroxypropylmethylcellulose (HPMC) are suitable. As the material for forming such gel, these compounds may be suitably mixed for use.

As the water to dissolve these material substances, ultra-pure water or deionized water may be used, however, ultra-pure water is particularly suitable. As the water, these may be suitably mixed for use.

Further, the pH of the buffer liquid is appropriately adjusted, depending upon the type of the sample to be electrophoretically separated. More specifically, in the case where the sample is a protein, the pH of the mother liquid is adjusted to an arbitrary suitable value in the range of 2 to 9, more preferably to an arbitrary suitable value in the range of 6.8 to 8.6. Further, in the case where the sample is a peptide, the pH of the mother liquid is adjusted to an arbitrary suitable value in the range of 2 to 11, more preferably to an arbitrary suitable value in the range of 2.5 to 3.1. Further, in the case where the sample is a nucleic acid, the pH of the mother liquid is adjusted to an arbitrary suitable value in the range of 6.8 to 9.2, more preferably to an arbitrary suitable value in the range of 7.5 to 8.5. However, it should be noted that there is the possibility that the ZnO fine particles may dissolve into the buffer under a strongly acidic condition (approx. pH 3 or lower). Therefore, when a peptide is used as the sample, it is preferable to use a buffer which has a pH value as close to neutrality (pH≅7) as possible. These points of attention are the same as those which are generally known for the electrophoresis.

The concentration of the hydrophilic gel in the buffer liquid is preferably an arbitrary suitable value in the range of 0.01 to 3 wt %. The concentration is determined mainly in consideration of the molecular weight, and the like, of the substance to be separated.

Further, the fluorescent dye to be used with the sample can be appropriately selected in accordance with the substance to be analyzed. At this time, it is preferable to use a fluorescent dye the excitation light for which will not excite the fine particles (ZnO or $TiO_2$) constituting the fine particle layer 20 (will not cause the fine particles to emit fluorescence). For example, in performing a DNA analysis, as the fluorescent dye, ethidium bromide, which is easy to bind to DNA, or a fluorescent dye having the same characteristic (for example, that with a brand name of SYBR GOLD, manufactured by Invitrogen) can be preferably used. Ethidium bromide emits fluorescence having a wavelength of 580 nm, being excited by light with a wavelength of 470 nm. SYBR GOLD emits fluorescence having a wavelength of 515 nm, being excited by light with a wavelength of 450 to 490 nm. Therefore, in the case where either of these fluorescent dyes is used, by detecting the light having a wavelength of that fluorescence, the DNA distribution, or the like, in the separation channel 14 can be observed.

The buffer liquid used with the technique disclosed in Patent Document 2 is mixed with ZnO fine particles, while, in the case where the micro-channel chip 10 is used for performing electrophoresis, there is no need for mixing ZnO fine particles into the buffer liquid. Therefore, the buffer liquid which has conventionally been used for electrophoresis can be adopted as it is.

In the same way as disclosed in Patent Document 2, by introducing the above-mentioned buffer liquid into the introduction channel 12 and the separation channel 14, and the sample to be analyzed into the sample reservoir 12a, respectively, and causing a potential gradient to be generated in the introduction channel 12 and the separation channel 14, a distribution of migration distances in accordance with, for example, the DNA chain lengths is produced in the long separation channel 14. At this time, if the excitation light for exciting the above-mentioned fluorescent dye bound to the DNA is irradiated onto the separation channel 14, the fluorescent dye will emit fluorescence.

At this time, a number of fine particles in the fine particle layer 20 formed on the inner faces of the separation channel 14 multiply reflect this excitation light, thereby the rate at which the fluorescent dye contained in the sample absorbs this excitation light being increased. Therefore, the intensity of the emitted fluorescence is also increased. This qualitative effect is the same as that which is obtained with the technique disclosed in Patent Document 2. However, as described later, in the case where the micro-channel chip 10 is used, a higher fluorescence intensity can be observed.

In addition, with the technique disclosed in Patent Document 2, if the distribution of the fine particles in the buffer liquid is not uniform, the distribution of fluorescence under observation is influenced not only by the distribution of DNA, and the like, as the measurement object, but also the distribution of the fine particles, thereby it becoming difficult to accurately calculate the distribution of DNA, and the like. Therefore, it is required to uniformly mixing the fine particles into the buffer liquid. However, actually, it is difficult to uniformly mix the fine particles into the highly viscous buffer liquid with a good reproducibility.

Contrarily to this, in the case where the above-mentioned micro-channel chip 10 is used, the buffer liquid which has been conventionally used can be adopted as it is. Further, formation of the fine particle layer 20 on the inner wall of the separation channel 14 can be easily performed by the aforementioned manufacturing method. In addition, this operation need to be made only once at the time of manufacturing the micro-channel chip 10. In addition, assuming that the fine particles were non-uniformly distributed, such distribution will not be varied so long as the fine particles are fixed. Therefore, by calculating the non-uniform distribution of the fine particles, and correcting the measured fluorescence distribution in consideration of the non-uniformity in distribution of the fine particles, more accurate distribution of DNA can be calculated.

In other words, use of the micro-channel chip 10 allows the fluorescence from the channel to be detected with high accuracy, whereby a highly accurate electrophoresis measurement can be performed. In addition, the micro-channel chip 10 can be easily used with a good reproducibility of the measurement, which allows automated measurement to be achieved with ease.

Figure 2:
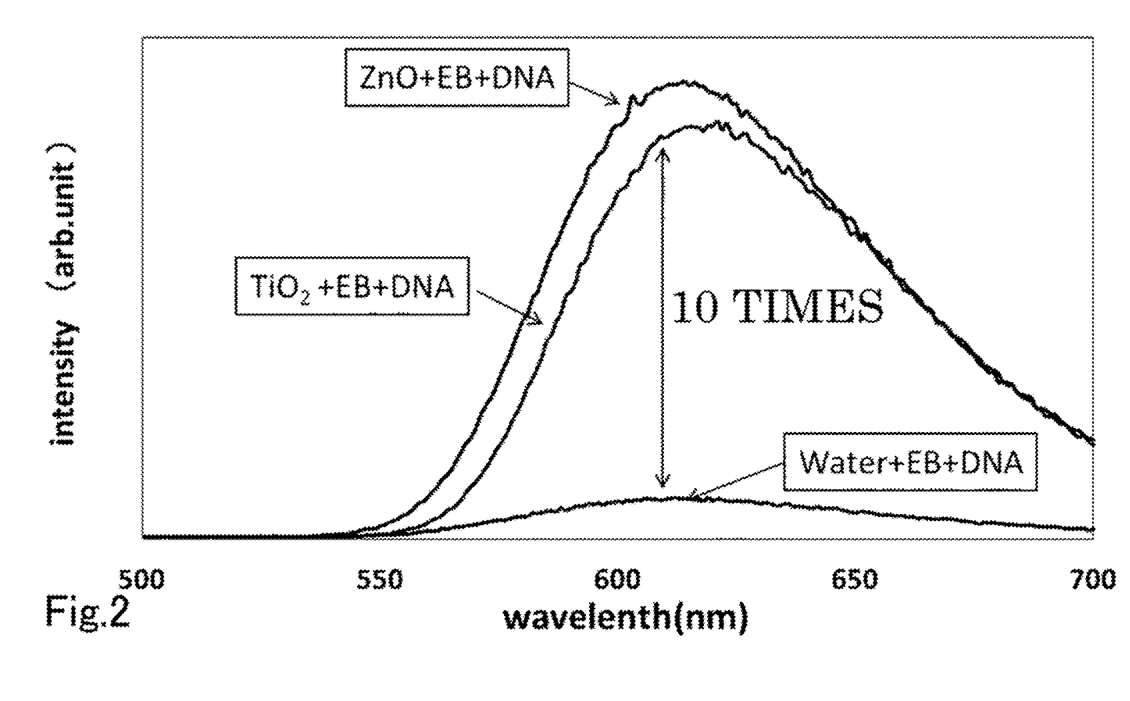
FIG. 2 shows a result of actual measurement of an emission spectrum from a liquid mixture of ethidium bromide (EB) and DNA to which ZnO fine particles or $TiO_2$ fine particles have been added.

Actually, the liquid dispersing the aforementioned fine particles was mixed with ethidium bromide (a fluorescent dye), and a DNA sample, and the luminescence intensity at an exciting wavelength of 480 nm was measured. Here, as the fine particles, ZnO fine particles having an average particle diameter of 200 nm, and $TiO_2$ fine particles with an average particle diameter of 80 nm were used, and by using an ultrasonic-wave homogenizer, these respective types of fine particles of 20 mg were dispersed in 1 ml of pure water to prepare a dispersion liquid. This dispersion liquid of 150 μl was added with 675 μl of ethidium bromide (EB) and 675 μl of DNA for performing measurement. FIG. 2 shows luminescence intensity spectra obtained in this test. Here, the result of a test in which pure water was added instead of the fine particles is given on the same graph. However, here, the reproducibility of the result in the case where either the ZnO fine particles or the $TiO_2$ fine particles were added is not good, and the result given in FIG. 2 is that which was obtained when the luminescence was at a maximum. From this result, it can be confirmed that, when either the ZnO fine particles or the $TiO_2$ fine particles were used, the light output was enhanced, and especially at a wavelength of 620 nm or so, a light intensity 10 times as high as that which can be obtained when neither of these types of fine particles was added can be obtained at maximum. In other words, as the above-mentioned fine particles, the ZnO fine particles and the $TiO_2$ fine particles are both effective.

Figure 3:
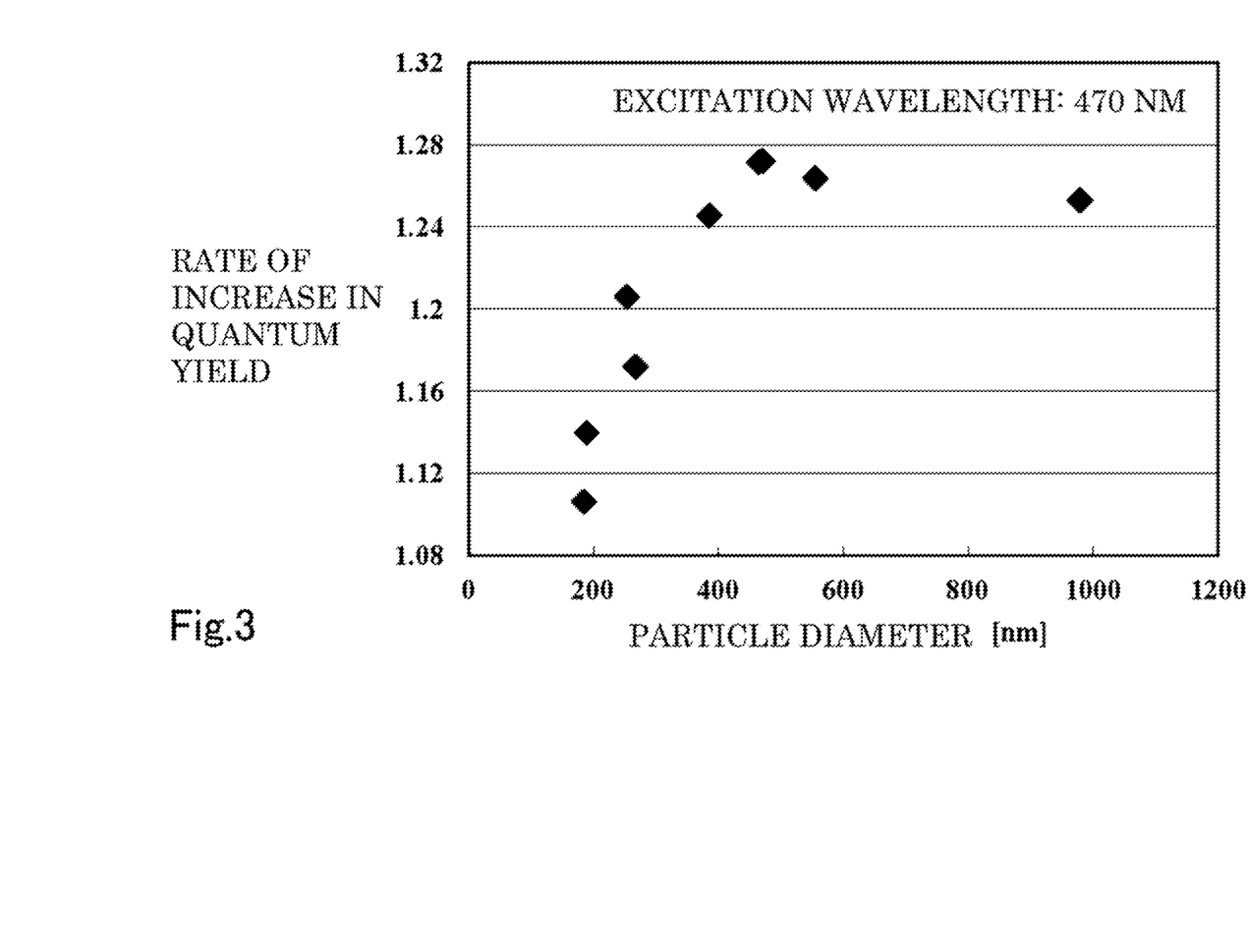
FIG. 3 shows a result of determination of the relationship between the rate of increase in quantum yield and the average particle diameter of the ZnO fine particles in case where the ZnO fine particles have been added.
Figure 4:
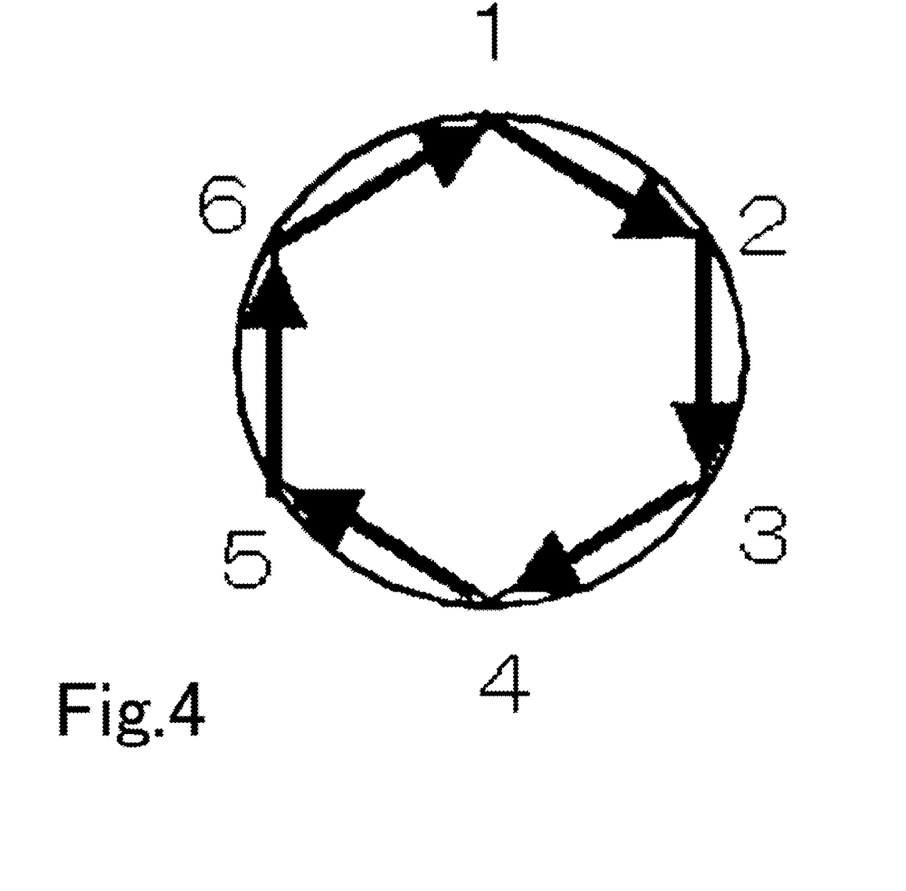
FIG. 4 is a figure schematically showing a cloister wave which is formed in a hexagonal columnar ZnO crystal.

In addition, the result of investigation of the relationship between the average particle diameter and the quantum yield for the above-mentioned test piece (using the ZnO fine particles) is given in FIG. 3. Here, the value of the vertical axis when the value of the horizontal axis is zero represents a quantum yield in the case where no fine particles are added, providing a standardized value. As can be seen from this result, the effect of sensitization provided by addition of the ZnO fine particles is enhanced at 400 to 500 nm, where the average particle diameter is substantially equal to the wavelength of the excitation light. Considering that the refractive index of ZnO is 2.0 or so, the wavelength of the excitation light at the ZnO fine particles is, in this case, approx. ⅙ of the length of the outer periphery of a ZnO fine particle. Therefore, as shown in FIG. 4, it is estimated that the excitation light constitutes a cloister wave in a hexagonal column-shaped ZnO crystal. Thereby, it is supposed that, especially at the surface of a ZnO fine particle, the electric field is enhanced, resulting in the fluorescence intensity being enhanced. Therefore, in the case where, as with ethidium bromide or SYBR GOLD, the excitation light having a wavelength of 400 to 500 nm is used, it is particularly preferable to use fine particles having an average particle diameter of 400 to 500 nm.

EXAMPLE

First, the above-mentioned micro-channel chip was actually manufactured. Here, on the inner faces of a channel which was machined to a geometry shown in FIG. 1 and to which a lid was joined, a fine particle layer constituted by ZnO fine particles was formed. Here, a coating liquid was used which was prepared by adding 20 mg of ZnO fine particles having an average particle diameter of 200 nm to 18 ml of pure water and 2 ml of sodium polyacrylate, and applying an ultrasonic wave to mix them. Such coating liquid was poured into the channel, and dried at 100° C., which was followed by calcination at 300° C. to fix the ZnO fine particles in the channel (separation channel, and the like). By performing this operation two times, the fine particle layer was formed.

Figure 5:
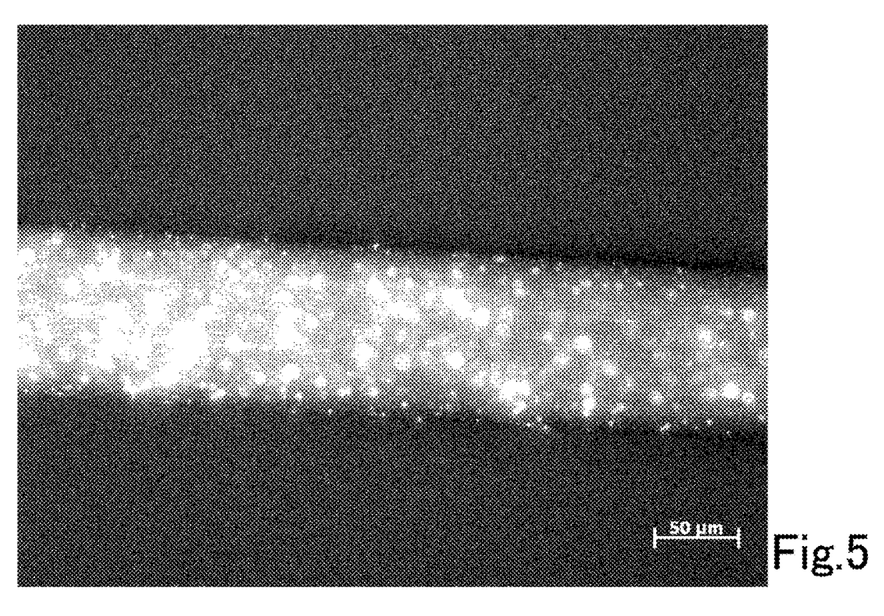
FIG. 5 is a result of photographing of fluorescence from ZnO in a test piece in which a ZnO fine particle layer is formed on the inner wall.

FIG. 5 shows a result of having photographed fluorescence with a wavelength of approx. 400 nm emitted by the ZnO fine particles when an ultraviolet light having a wavelength of 365 nm was irradiated thereonto in this state. Thereby, it can be confirmed that the ZnO fine particles are uniformly fixed in the channel. In the case where light having a wavelength of 450 to 490 nm that provides an excitation light for SYBR GOLD for use as a color developing substance was irradiated, there was observed no fluorescence. From this result, it was confirmed that the fluorescence emitted by the ZnO will have no influence on the luminescence from the SYBR GOLD.

Figure 6:
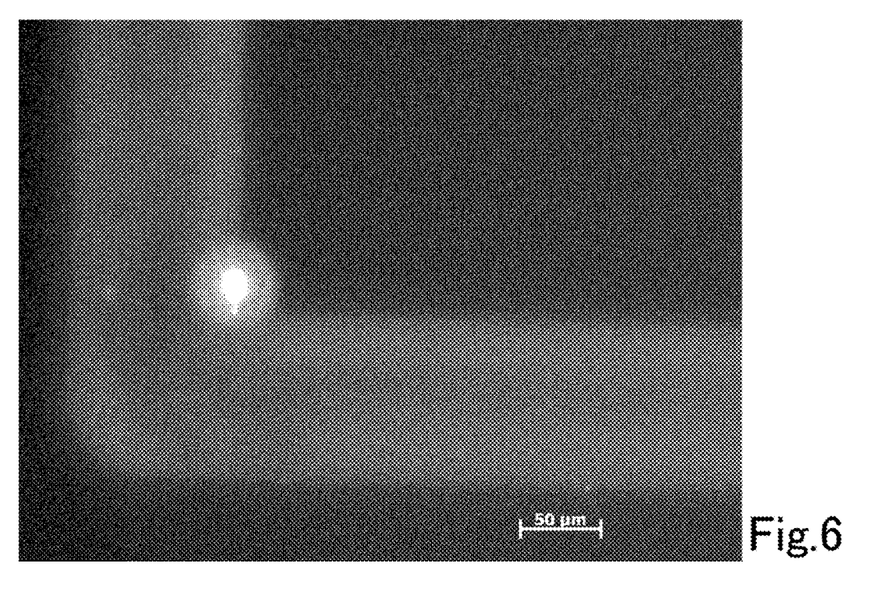
FIG. 6 is a result of photographing of fluorescence from SYBR GOLD in a test piece in which a ZnO fine particle layer is not formed on the inner wall (Comparative Example)
Figure 7:
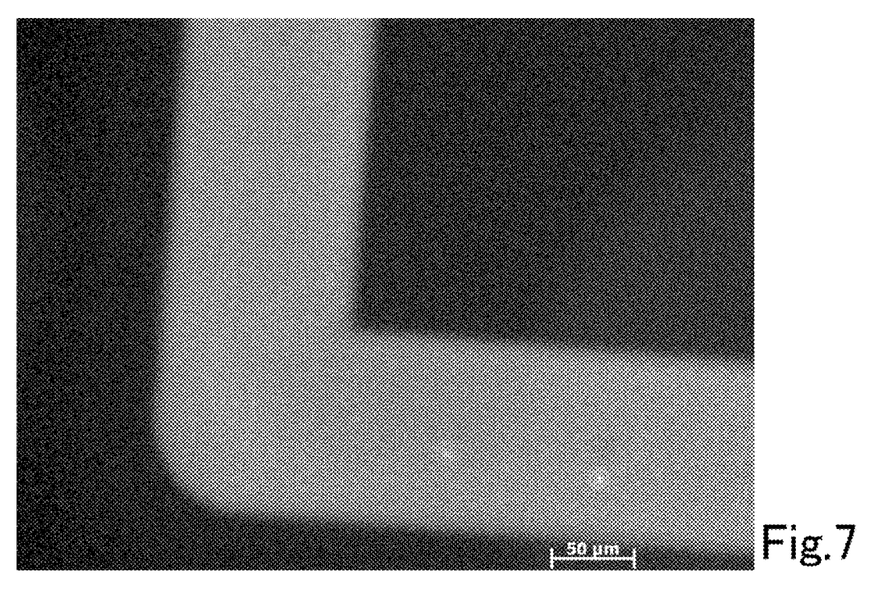
FIG. 7 is a result of photographing of fluorescence from SYBR GOLD in a test piece in which a ZnO fine particle layer is formed on the inner wall (Example)

Next, FIG. 6 shows a result of having photographed luminescence of fluorescence (green) having a wavelength of 515 nm when, in the state in which no fine particle layer was formed (Comparative Example), a buffer liquid containing SYBR GOLD was fed into the channel, and then light having a wavelength of 450 to 490 nm, which provides an excitation light, was irradiated thereonto. Further, FIG. 7 shows a result of having photographed in the same manner in the state in which a fine particle layer was formed in the channel as described above (Example). From this result, it can be confirmed that the existence of the fine particle layer uniformly enhanced the fluorescence. From the aforementioned result, since this luminescence does not contain the light which was emitted by the ZnO itself, this result indicates that the fluorescence itself which was emitted by the SYBR GOLD was enhanced by the fine particle layer. Moreover, unlike the case where the fine particles were directly mixed into the buffer liquid, the reproducibility of enhancement of the fluorescence was good.

Next, there will be explained a result of actually having performed electrophoresis about DNA, using (1) a micro-channel chip in which no fine particle layer was formed (Comparative Example), (2) a micro-channel chip in which the above-mentioned fine particle layer was formed (Example), and a DNA 1000 kit manufactured by Shimazu Corporation. Here, as the buffer liquid, a buffer liquid which is generally used, being added with no fine particles, was used as it was, i.e., the same buffer liquid as that used in Experiment A disclosed in Patent Document 2 was used.

Figures 8A, 8B:
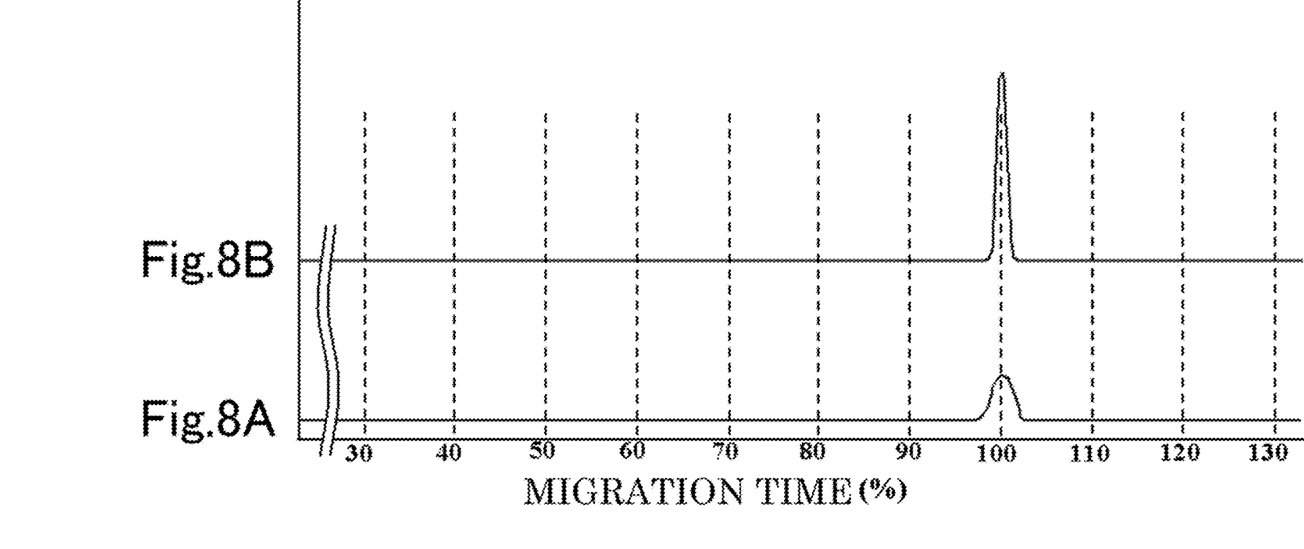
FIGS. 8A, 8B depict a detection intensity of fluorescence obtained when electrophoresis of DNA was performed using a micro-channel chip of Comparative Example (a) and that of Example (b), respectively.

FIG. 8 gives actual measurements of the migration time (corresponding to the migration distance) and the fluorescence intensity (corresponding to the DNA detection sensitivity). Here, (a) in FIG. 8 represents the actual measurement for Comparative Example, while (b) represents that for Example. The result represented by (a) in FIG. 8 is the same as that which was obtained in Experiment A in Patent Document 2. In Example, a sensitivity five or more times as high as that in Comparative Example has been obtained. In addition, in Example, it can be confirmed that, in the ordinate (fluorescence intensity), a great value has been given, and at the same time, the half-value width of the fluorescence intensity detected is decreased. This half-value width corresponds to the resolution of the molecular weight or the DNA chain length. In other words, the detection sensitivity has been enhanced, and at the same time, the resolution has also been enhanced. The reason why the resolution is enhanced is that the efficiency of taking out the light from the channel is increased, thereby the light in an area where the excitation light has been irradiated being detected with a good efficiency, and in the area other than the excited one, the luminescence due to multiple reflection of the light which has not been taken out being minimized.

In Patent Document 2, the result obtained in Example in Patent Document 2 is disclosed in Table 3, and the like, as Experiment C, and the detection sensitivity was approx. 2.4 times as high as that in Comparative Example (Experiment A). Accordingly, in Example stated in the present application, a detection sensitivity which is still higher than this has been obtained. The reason for this can be considered to be that the excitation light was more easily multiply-scattered in the case where the fine particles were dispersed in the inner wall than in the case where the fine particles were dispersed in the liquid.

Accordingly, it has been confirmed that using the micro-channel chip of Example allows the same buffer liquid as conventional one, and the like, to be adopted for performing electrophoretic measurement with high accuracy.

Figure 9:
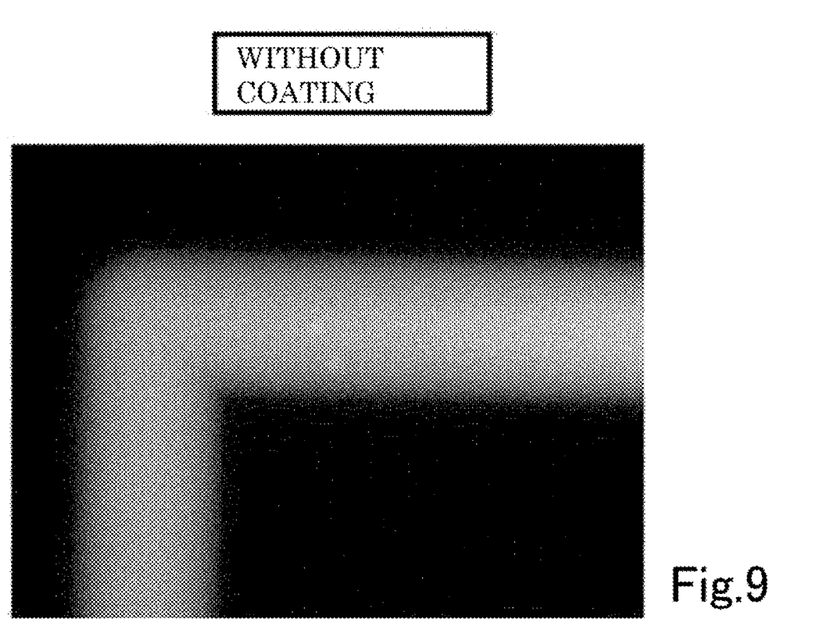
FIG. 9 is a result of photographing of fluorescence from SYBR GOLD in a test piece in which a $TiO_2$ fine particle layer is not formed on the inner wall (Comparative Example)
Figure 10:
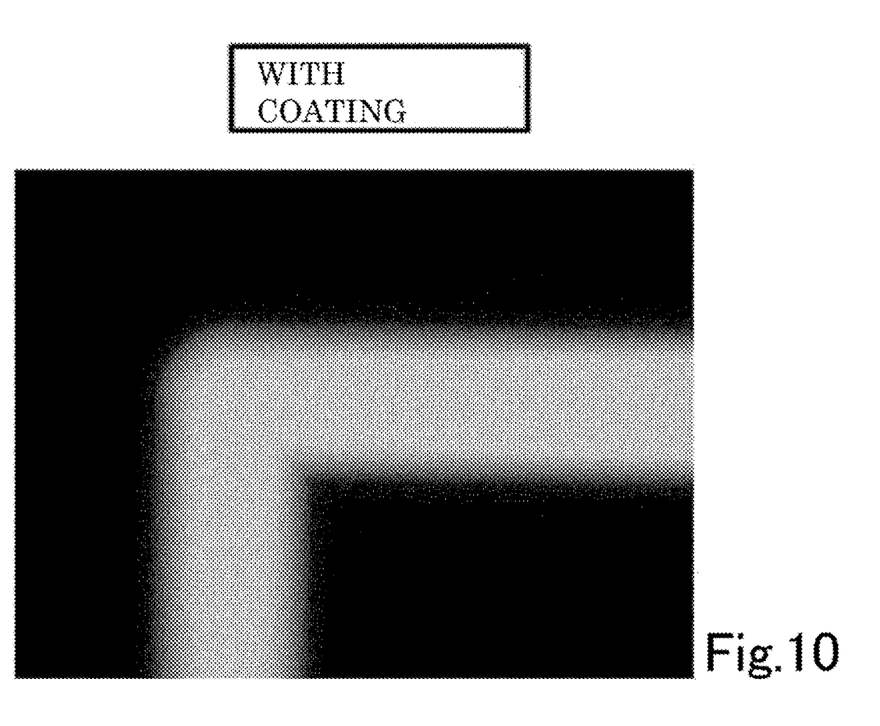
FIG. 10 a result of photographing of fluorescence from SYBR GOLD in a test piece in which a $TiO_2$ fine particle layer is formed on the inner wall (Example).

Next, Example in the case where, instead of the ZnO fine particles, $TiO_2$ fine particles are used will be explained. Here, instead of the aforementioned ZnO fine particles, $TiO_2$ fine particles having an average particle diameter of 80 nm were used to perform the same measurement as that in FIG. 7. FIG. 9 shows luminescence in the case where the $TiO_2$ fine particles were not coated, while FIG. 10 shows the result in the case where the $TiO_2$ fine particles were coated. It can be confirmed that, even in the case where the $TiO_2$ fine particles were coated, the luminescence intensity was increased.

In the above-mentioned example, as the fluorescent dye, SYBR GOLD was used, however, even in the case where ethidium bromide was used, the same result was obtained. In addition, in the above-mentioned example, the micro-channel chip, which is Example of the present invention, was used in the DNA analysis, however, from the principle of the electrophoresis method, it is obvious that, even in analysis of other molecules, the above-mentioned micro-channel chip is effective.

In addition, the method for forming a fine particle layer on the inner wall of the channel is not limited to the method which uses an aqueous solution as described above, and is arbitrarily selectable. It is obvious that, so long as the existence of the fine particles has no influence on the migration of a molecule, the same advantages are provided.

In addition, in the above-mentioned example, an example in which this micro-channel chip was used for electrophoresis has been described, however, in detecting the fluorescence emitted from a fluorescent dye in the liquid existing in a channel, it is obvious that the above-mentioned configuration is effective. Accordingly, the application for the above-mentioned micro-channel chip is not particularly limited to electrophoresis. In this case, for example, the electrode for generating an electric field in the liquid in the channel is not always required.

DESCRIPTION OF SYMBOLS

The symbol 10 denotes a micro-channel chip; 11 a plate-like body; 12 an introduction channel; 12a a sample reservoir; 12b an outlet; 14 a separation channel; 14a a buffer injection port; 14b a buffer storage hole; 16 an intersection portion; 20 a fine particle layer; and 30 a lid.

The invention claimed is:

1. A micro-channel chip, comprising a channel, the channel being provided for introducing a liquid containing a fluorescent dye therein, and having a configuration allowing light emitted by said fluorescent dye to be observed from outside,
   wherein a fine particle layer composed of fine particles having an average particle diameter of 80 to 500 nm and mainly made of zinc oxide (ZnO) or titanium oxide ($TiO_2$), is formed on an inner wall of said channel.

2. The micro-channel chip according to claim 1, wherein said channel is configured by using a groove formed within a substrate which is transparent to an excitation light irradiated onto said fluorescent dye.

3. The micro-channel chip according to claim 2, wherein there is provided a configuration in which an electric field is applied to a liquid in said channel.

4. The micro-channel chip according to claim 2, wherein the wavelength of the excitation light irradiated onto said fluorescent dye is in the range of 400 to 500 nm, and the average particle diameter of said fine particles is in the range of 400 to 500 nm.

5. The micro-channel chip according to claim 1, wherein there is provided a configuration in which an electric field is applied to a liquid in said channel.

6. The micro-channel chip according to claim 5, wherein the wavelength of the excitation light irradiated onto said fluorescent dye is in the range of 400 to 500 nm, and the average particle diameter of said fine particles is in the range of 400 to 500 nm.

7. The micro-channel chip according to claim 1, wherein the wavelength of the excitation light irradiated onto said fluorescent dye is in the range of 400 to 500 nm, and the average particle diameter of said fine particles is in the range of 400 to 500 nm.

* * * * *